United States Patent
Park et al.

(10) Patent No.: US 11,097,104 B2
(45) Date of Patent: Aug. 24, 2021

(54) ELECTROPORATION DEVICE AND A METHOD FOR CONTROLLING AN ELECTROPORATION DEVICE

(71) Applicant: L'OREAL, Paris (FR)

(72) Inventors: Woo Ram Park, Kawasaki (JP); Chin Kai Lee, Kawasaki (JP); Bradford Pistorio, Clark, NJ (US); Jinghua Nan, Kawasaki (JP)

(73) Assignee: L'Oreal, Paris (FR)

( * ) Notice: Subject to any disclaimer, the term of this patent is extended or adjusted under 35 U.S.C. 154(b) by 14 days.

(21) Appl. No.: 16/344,753

(22) PCT Filed: Jul. 14, 2017

(86) PCT No.: PCT/JP2017/026586
§ 371 (c)(1),
(2) Date: Apr. 24, 2019

(87) PCT Pub. No.: WO2018/078973
PCT Pub. Date: May 3, 2018

(65) Prior Publication Data
US 2019/0329035 A1    Oct. 31, 2019

(30) Foreign Application Priority Data
Oct. 26, 2016 (JP) .............................. JP2016-209380

(51) Int. Cl.
*A61N 1/36* (2006.01)
*A61B 5/0531* (2021.01)
(Continued)

(52) U.S. Cl.
CPC ........ *A61N 1/36031* (2017.08); *A61B 5/0531* (2013.01); *A61N 1/0412* (2013.01);
(Continued)

(58) Field of Classification Search
None
See application file for complete search history.

(56) References Cited

U.S. PATENT DOCUMENTS

| | | |
|---|---|---|
| 5,983,131 A | 11/1999 | Weaver et al. |
| 6,654,636 B1 | 11/2003 | Dev et al. |

(Continued)

FOREIGN PATENT DOCUMENTS

| | | |
|---|---|---|
| CN | 203451533 U | 2/2014 |
| JP | 03-502416 A | 6/1991 |

(Continued)

OTHER PUBLICATIONS

International Search Report dated Nov. 8, 2017, issued in corresponding International Application No. PCT/JP2017/026586, filed Jul. 14, 2017, 4 pages.

(Continued)

*Primary Examiner* — Kennedy Schaetzle
(74) *Attorney, Agent, or Firm* — Christensen O'Connor Johnson Kindness PLLC

(57) ABSTRACT

The present invention provides an electroporation device and a method for controlling an electroporation device for facilitating delivering active substances into skin such as stratum corneum while minimizing discomfort of a user by modulating applied voltage pulses. The electroporation device according to the present invention comprises: a measurement unit being configured to provide multiple outputs of one or more resistance measurement voltage pulses for measuring a resistance of skin of a user at a predetermined interval; and an output unit being configured to provide an output of one or more electroporation voltage pulses to the skin of the user based on the resistance of the skin of the user per each output of the one or more resistance measurement voltage pulses.

20 Claims, 3 Drawing Sheets

(51) Int. Cl.
*A61N 1/04* (2006.01)
*A61N 1/32* (2006.01)

(52) U.S. Cl.
CPC ......... *A61N 1/327* (2013.01); *A61N 1/36014* (2013.01); *A61N 1/36021* (2013.01); *A61N 1/36034* (2017.08)

(56) References Cited

U.S. PATENT DOCUMENTS

| | | | |
|---|---|---|---|
| 8,048,067 B2 * | 11/2011 | Davalos | A61B 18/12 606/32 |
| 2004/0039327 A1 | 2/2004 | Miklavcic et al. | |
| 2007/0232984 A1 | 10/2007 | Lovell et al. | |
| 2008/0091135 A1 * | 4/2008 | Draghia-Akli | A61N 1/0412 604/20 |
| 2010/0030211 A1 * | 2/2010 | Davalos | A61N 1/327 606/41 |
| 2012/0323165 A1 * | 12/2012 | Broderick | A61N 1/327 604/20 |
| 2013/0030430 A1 * | 1/2013 | Stewart | A61B 18/1492 606/41 |
| 2019/0117964 A1 * | 4/2019 | Bahrami | A61N 1/327 |
| 2020/0297418 A1 * | 9/2020 | Stewart | A61B 18/1492 |

FOREIGN PATENT DOCUMENTS

| | | |
|---|---|---|
| JP | 2003-502416 A | 6/1991 |
| JP | 2010-506660 A | 3/2010 |
| WO | 89/006555 A1 | 7/1989 |
| WO | 89/06555 A1 | 7/1989 |
| WO | 2008/048632 A1 | 4/2008 |
| WO | 2016/161201 A2 | 10/2016 |

OTHER PUBLICATIONS

Notice of Reasons for Rejection dated Jul. 6, 2020, issued in corresponding Japanese Application No. 2016-209380, 7 pages.

* cited by examiner

ELECTROPORATION DEVICE AND A METHOD FOR CONTROLLING AN ELECTROPORATION DEVICE

FIELD OF INVENTION

The present invention relates to an electroporation device for applying electric pulses to skin to introduce substances into the skin and a method for controlling an electroporation device.

BACKGROUND OF THE INVENTION

In a field of beauty care, various methods are proposed to introduce various molecules into a human skin. One example of such methods is an ionic introduction method. The ionic introduction method is a method for introducing various substances provided onto a human skin into the inside of the skin such as a stratum corneum by applying a voltage. Vitamin C derivatives such as an ascorbic acid generally have a negative charge. Therefore, when an aqueous solution including an ascorbic acid is provided onto skin and a negative voltage is applied to the portion where the solution is provided, the ascorbic acid is moved into the skin by the electrostatic repulsion force.

However, the ionic introduction method has a problem that the substances to be introduced into skin must be ionic molecule. Furthermore, the ionic introduction method has another problem in which molecules having a large molecular mass cannot be introduced because the mechanism of the delivery of substances into skin is infiltration between skin cells. Therefore, the ionic introduction method is not suitable to introduce substances having a large molecular mass such as a collagen and hyaluronic acid.

In order to solve the above problems, an electroporation method is proposed. The electroporation method comprises applying voltage pulses to skin after substances to be introduced into the skin are provided onto the skin. Since applying voltage pulses makes microscopic holes in the skin, the provided substances are introduced into the skin via the microscopic holes. The holes are cured and filled in a short time because the holes are extremely small. Therefore, electroporation has a capacity of introducing even electrically neutral molecules of substances into skin in contrast to the ionic introduction method. Since substances are introduced via holes made in skin instead of just infiltration, molecules having a larger molecule mass can be introduced compared with the ionic introduction method.

However, the electroporation method has a problem of discomfort for a user due to applying voltage pulses. The higher the voltage of the applied pulses is, the more holes are made on the skin and the larger the size of the holes is, and this results in more efficient introduction of substances into the skin. On the other hand, the higher the voltage of the applied pulses is, the more current is applied to the skin, and this results in discomfort for a user such as stimulation, irritation, or a pain sensation. Therefore, conventional methods have employed applying voltage pulses to skin of a user based on output pattern data which are the voltage heights of the pulses. The voltage heights are preliminarily determined based on data of measured electric resistance values of skin.

The electric resistance values of the skin are, however, not necessarily constant and are different with each person due to influences of moisture and fat included in skin. Even in the same person, the electric resistance value of the skin is variable due to the variation of moisture included in the skin affected by temperature and humidity of air and variations of other conditions of the surface of the skin. Since the voltage of pulses are generally set as high as possible in order to maximize the efficiency of the introduction of substances into the skin, the user may feel a pain sensation even applying the same voltage pulses if the electric resistance value of the skin varies.

SUMMARY OF THE INVENTION

Technical Problem to be Solved

The present invention provides an electroporation device and a method for controlling an electroporation device for modulating voltage pulses to be applied in order to minimize the discomfort of a user and facilitate delivering active substances inside the skin, such as a stratum corneum or epidermis.

Means for Solving the Problem

For solving the above technical problem, an electroporation device of the present invention comprises:

a measurement unit being configured to provide multiple outputs of one or more resistance measurement voltage pulses for measuring an electric resistance of skin of a user at a predetermined interval; and an output unit being configured to provide an output of one or more electroporation voltage pulses to the skin of the user based on the resistance of the skin of the user per each output of the one or more resistance measurement voltage pulses.

In the electroporation device of the present invention, the measurement unit may be configured to provide multiple outputs of one resistance measurement voltage pulse at a predetermined interval, and the output unit may be configured to provide an output of one electroporation voltage pulse per output of the one resistance measurement voltage pulse.

In the electroporation device of the present invention, the output unit may be configured to output the electroporation voltage pulses after varying at least one of a voltage, a pulse duration, an interval between pulses, a number of pulses, and a pulse duty ratio of the electroporation voltage pulse based on the resistance measured by the measurement unit.

In the electroporation device of the present invention, the output unit may be configured to output the electroporation voltage pulses after varying the voltage of the electroporation voltage pulse based on the resistance measured by the measurement unit.

In the electroporation device of the present invention, the output unit may be configured to output the electroporation pluses after varying the voltage of the electroporation voltage pulse based on the electric resistance measured by the measurement unit such that a current applied on the skin of the user by the electroporation voltage pulses is set to be a predetermined value.

In the electroporation device of the present invention, the output unit may be configured to output the electroporation voltage pulses after varying the voltage of the electroporation voltage pulses in a stepwise manner.

In the electroporation device of the present invention, the output unit may be configured to output the electroporation voltage pulses after varying the voltage of the electroporation voltage pulses in a continuous manner.

In the electroporation device of the present invention, the output unit may be configured to output the electroporation voltage pulses after varying the voltage of the electroporation voltage pulses within a range between 5 to 100 V.

In the electroporation device of the present invention, the measurement unit may be configured to output the resistance measurement voltage pulses having a voltage lower than a voltage of the electroporation voltage pulse.

In the electroporation device of the present invention, the measurement unit may be configured to output the resistance measurement voltage pulses to the skin of the user via a first electrode, and the output unit may be configured to output the electroporation voltage pulses to the skin of the user via a second electrode.

In the electroporation device of the present invention, the measurement unit and the output unit may be configured to output the resistance measurement voltage pulses and the electroporation voltage pulses to the skin of the user via a common electrode, respectively.

The electroporation device of the present invention may further comprise a timing unit being configured to output timing instructions for outputting the resistance measurement voltage pulses and the electroporation voltage pulses to the measurement unit and the output unit.

For solving the above technical problem, a method for controlling an electroporation device comprises a plurality of steps, each step comprising:

outputting a resistance measurement voltage pulse to skin of a user for measuring an electric resistances of the skin of the user one or more times; and determining parameters of an electroporation voltage pulse for outputting to the skin of the user one or more times based on the measured electric resistance.

In the method for controlling the electroporation device of the present invention, the electric resistance of the skin of the user may be measured once and the parameters of the electroporation voltage pulse may be determined once in each step.

In the method for controlling the electroporation device of the present invention, at least one of a voltage, a pulse duration, an interval between pulses, a number of pulses, and a pulse duty ratio among the parameters of the electroporation voltage pulse may be varied based on the measured electric resistance.

In the method for controlling the electroporation device of the present invention, the voltage of the electroporation voltage pulse may be varied based on the measured electric resistance.

In the method for controlling the electroporation device of the present invention, the voltage of the electroporation voltage pulse may be varied such that a current applied onto the skin of the user by the electroporation voltage pulse is set to be a predetermined value.

In the method for controlling the electroporation device of the present invention, the voltage of the electroporation voltage pulse may be varied in a stepwise manner.

In the method for controlling the electroporation device of the present invention, the voltage of the electroporation voltage pulse may be varied in a continuous manner.

In the method for controlling the electroporation device of the present invention, the voltage of the electroporation voltage pulse may be varied within a range between 10 and 50 V.

In the method for controlling the electroporation device of the present invention, a voltage of the resistance measurement voltage pulse may be lower than a voltage of the electroporation voltage pulse.

In the method for controlling the electroporation device of the present invention, the resistance measurement voltage pulses and the electroporation voltage pulses may be output in accordance with timing instructions output by a timing unit.

BRIEF DESCRIPTION OF THE DRAWINGS

Further features and advantages of the present invention will be apparent by referring to the embodiments disclosed in the following detailed description of the invention and the accompanying drawings.

EMBODIMENTS

An electroporation method is a technology for introducing active substances inside of the skin; For example, with stratum corneum by applying voltage pulses to the skin to form microscopic holes in the skin. Thus, a higher voltage of the pulse is able to deliver the substrates more efficiently into the skin. However, the electroporation method provides a decrease of an electric resistance of the skin. The decrease of the electric resistance of the skin results from a decrease of a barrier function of the stratum corneum. Conventional electroporation devices apply a constant voltage to the skin regardless of the electric resistance of the skin. Therefore, when the electric resistance of the skin is high, an output current becomes lower and results in a decrease of an efficiency of introducing substances. On the other hand, when the electric resistance of the skin is low, the output current becomes higher and results in an increase of the efficiency of introducing substances but the user feels a stronger discomfort such as stimulation, irritation, or a pain sensation. Therefore, it is necessary to control the voltage of the pulses as much as possible within a range in which the user does not feel or can accept the discomfort but having maximum efficacy.

The present invention provides an electroporation device and a method for controlling an electroporation device for measuring an electric resistance of skin of a user in real time and determining parameters of an electroporation voltage pulse output to the skin. Based on the measured electric resistance of the skin, in order to improve an efficiency of an introduction of substances into the skin of the user within a range in which the user does not feel or can accept the discomfort such as stimulation, irritation, or a pain sensation.

Figure 1:
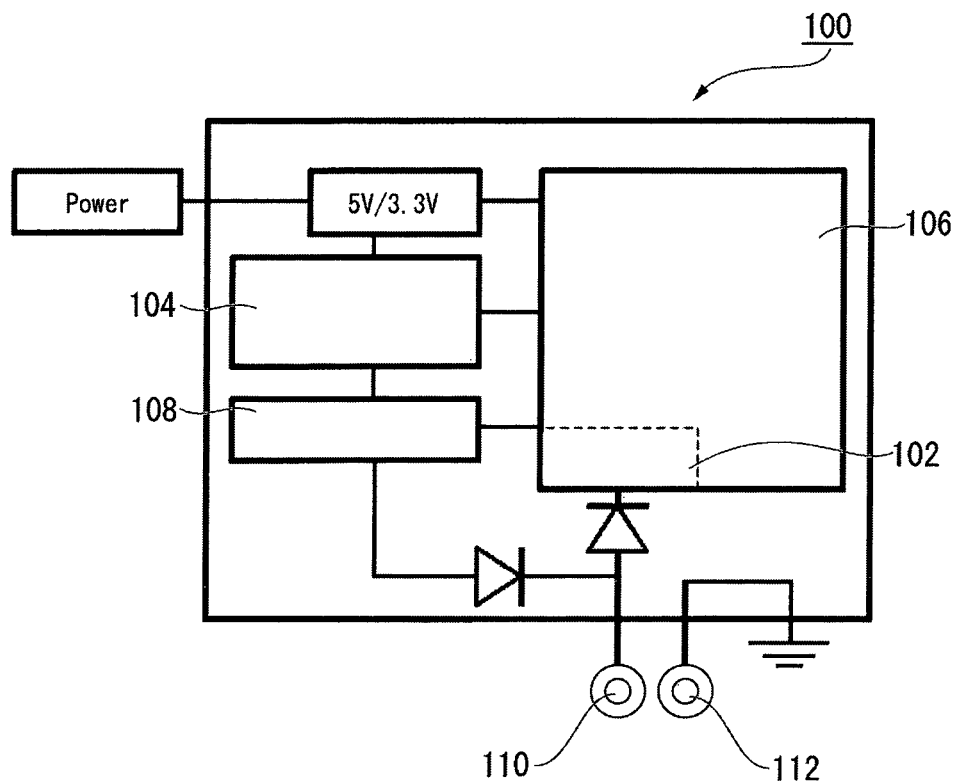
FIG. 1 shows an illustrative configuration of an electroporation device according to an embodiment of the present invention.

FIG. 1 shows an illustrative configuration of an electroporation device 100 according to an embodiment of the present invention. The electroporation device 100 comprises a measurement unit 102 for measuring an electric resistance of skin and an output unit 104 for outputting electroporation voltage pulses. The electroporation device 100 may comprise a microprocessor 106 for controlling the measurement unit 102 and the output unit 104, a timing unit 108, a first electrode 110, and a second electrode 112. At least one of the measurement unit 102, the output unit 104, and the timing unit 108 may be incorporated in the microprocessor 106. Although FIG. 1 shows the electroporation device 100 incorporating the measurement unit 102 in the microprocessor 106, such a configuration does not limit embodiments of the present invention.

Figure 2:
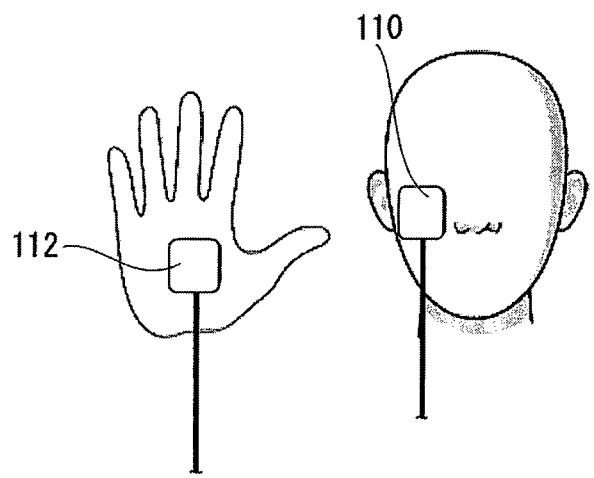
FIG. 2 shows a situation in which electrodes of the electroporation device according to the embodiment of the present invention are attached to a user.

FIG. 2 shows a situation in which the first and second electrodes 110, 112 of the electroporation device 100 shown in FIG. 1 are attached to a body of the user. The first electrode 110 is attached to a position for introducing an active substance by the electroporation method, for example, a cheek, and the second electrode 112 is attached to a position different from the position to which the first electrode 110 is attached, for example, a palm. Forming the first and second electrodes 110, 112 in a shape of a tape or a patch helps to be easily attached to the skin of the user.

The measurement unit 102 outputs and applies one or more resistance measurement voltage pulses to the skin of the user via the first electrode 110. After outputting the resistance measurement voltage pulses, the measurement unit 102 measures an electric resistance value of the skin by using various methods described below based on a potential difference between the first and second electrodes 110, 112.

Figure 3:
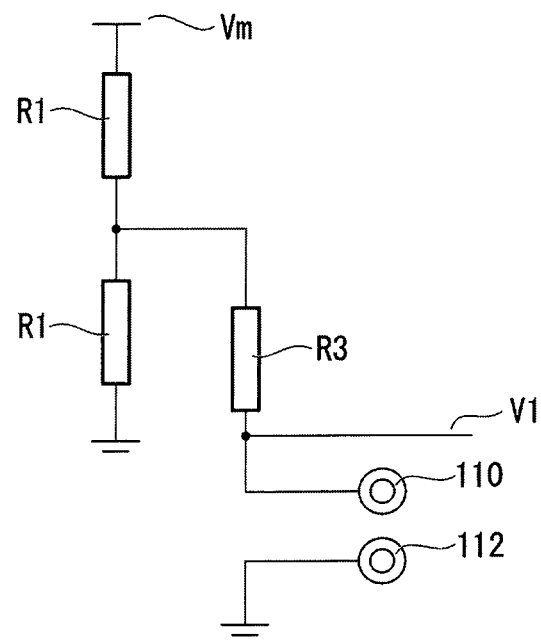
FIG. 3 shows a schematic example of a circuit of the electroporation device according to the embodiment of the present invention for measuring an electric resistance value of skin.

FIG. 3 shows a schematic example of a circuit for measuring the electric resistance value of the skin by the resistance measurement voltage pulse. A first resistor R1 and a second resistor R2 are serially connected between an output voltage Vm of the resistance measurement voltage pulse of the measurement unit 102 and a ground potential and a third resistor R3 is connected to a point between the first and second resistors R1, R2. Further, the first electrode 110 is serially connected to the third resistor R3. The second electrode 112 is connected to the ground potential. When the first and second electrodes 110, 112 are attached to the user as shown in FIG. 2, the resistor Rskin of the skin of the user is connected between the first and second electrodes 110, 112 of FIG. 3. The output voltage Vm of the measurement unit 102 is divided by the first and second resistors R1, R2, and a potential between the first and second resistors R1, R2 is denoted by V0. The potential V0 is further divided by the third resistor R3 and the skin resistor Rskin, and a potential between the third resistor R3 and the first electrode 110 is denoted by V1. By measuring V1, an electric resistance value of the skin resistor Rskin is obtained. However, methods for measuring the electric resistance value of the skin by the measurement unit 102 are not limited to the circuit configuration shown in FIG. 3, but bridge circuits such as a wheatstone bridge and other various methods for measuring an electric resistance can be employed.

After the measurement unit 102 measures the electric resistance value of the skin, the output unit 104 determines parameters of an electroporation voltage pulse for the electroporation method based on the measured electric resistance value of the skin. The parameters to be determined may be at least one of a voltage, a pulse duration, an interval between pulses, a number of pulses, and a pulse duty ratio of the electroporation voltage pulse. As described above, a discomfort such as a pain sensation caused by applying the electroporation voltage pulses mainly results from a current applied to the skin. Therefore, it is advantageous to determine the voltage of the electroporation voltage pulse such that the current is maintained at a predetermined value lower than a value at which the user feels the discomfort. The voltage of the electroporation voltage pulse can be set to be, for example, 100 V or less, or for example, between 10 and 50 V. The voltage of the resistance measurement voltage pulse should be set to be sufficient to measure the electric resistance value of the skin but not to vary the electric resistance value of the skin. Therefore, while the electroporation voltage pulse is generally output at a voltage of 100 V or less, the voltage of the resistance measurement voltage pulse may be lower than that of the electroporation voltage pulse, for example, 10 V or less, or for example, 1 V or less.

FIGS. 1 to 3 show, a configuration in which the resistance measurement voltage pulse and the electroporation voltage pulse are output via the common electrode 110. However, an electrode, to which the resistance measurement voltage pulses, may be different from an electrode to which the electroporation voltage pulses.

The voltage of the electroporation voltage pulse can be determined, for example, by using an analog multiplying circuit for multiplying the measured electric resistance value of the skin and the current value described above preliminarily set. Alternatively, the voltage of the electroporation voltage pulse can be determined by converting the measured electric resistance value to a digital value by using an analog-digital converter and processing the digital value by the microprocessor 106. These methods can determine the voltage of the electroporation voltage device as a substantially continuous value.

Figure 4:
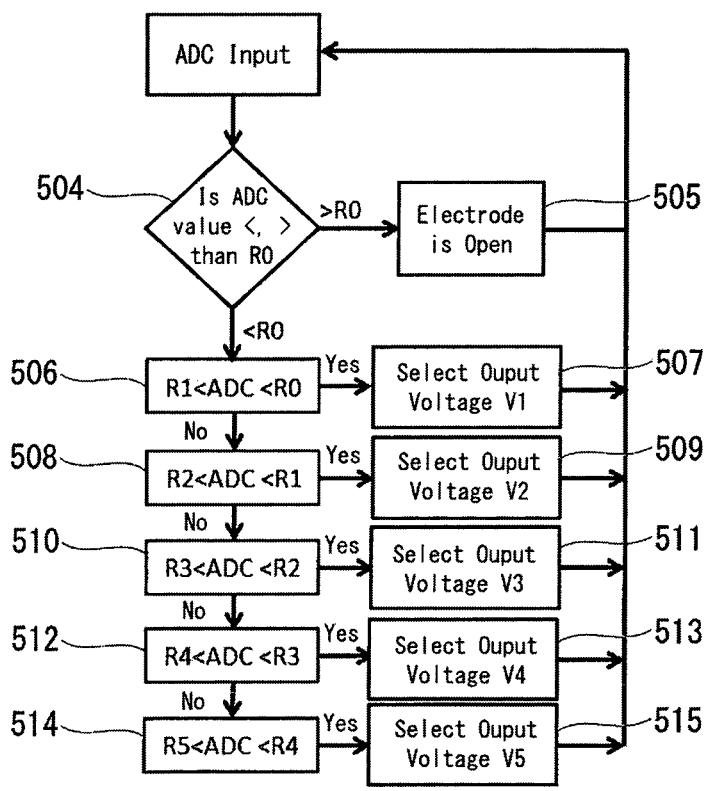
FIG. 4 shows an example of a flow diagram for determining a voltage of an electroporation voltage pulse of the electroporation device according to the embodiment of the present invention.

Alternatively, a voltage corresponding to a comparator circuit matching with a comparing condition can be determined as the voltage of the electroporation voltage pulse by comparing the measured electric resistance value of the skin with a preliminarily set threshold value of each of a plurality of comparator circuits. FIG. 4 shows a schematic flow diagram for determining the voltage of the electroporation voltage pulse by using comparator circuits.

Figure 5:
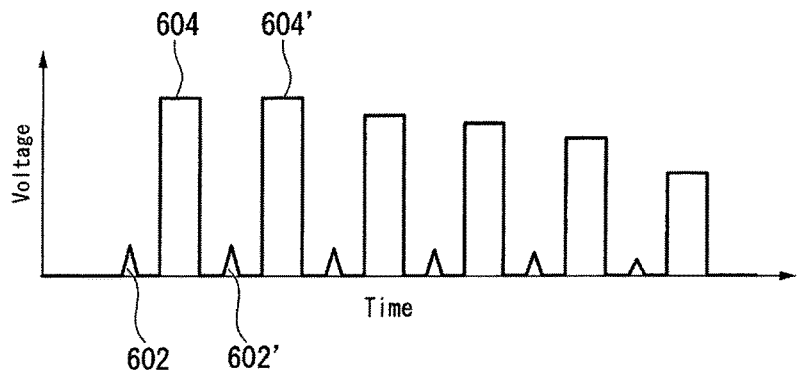
FIG. 5 shows illustrative outputs of resistance measurement voltage pulses and electroporation voltage pulses of the electroporation device according to the embodiment of the present invention.

In FIG. 4, the electric resistance value of the skin measured by the measurement unit 102 is converted to a digital value by an analog-digital converter (step 402). Then, it is determined whether or not the measured electric resistance value is larger than a predetermined resistance value Rx (step 404). If the measured electric resistance value is larger than Rx, it is determined that the electrodes are in an open state, i.e., at least one of the first and second electrodes 110, 112 is not attached to the skin of the user (step 405), then the process returns to a measurement of the electric resistance value of the skin by the measurement unit 102. If the measured electric resistance value is smaller than Rx, a first comparator determines whether or not the measured electric resistance value is larger than a predetermined electric resistance value Ra (step 406). If the measured electric resistance value is larger than Ra, the voltage of the electroporation voltage pulse is determined to be Va (step 407). If the measured electric resistance is smaller than Ra, a second comparator circuit determines whether or not the measured electric resistance value is larger than a predetermined electric resistance value Rb (408). In the following steps, the measured resistance value is compared with a predetermined resistance value of a comparator circuit and it is determined whether the voltage of the electroporation voltage pulse is set or the process proceeds to the next comparator circuit similarly to the above steps. The example shown in FIG. 5 comprises the five comparator circuits and therefore a voltage can be determined among five voltage values as the electroporation voltage pulse in a stepwise manner. Although FIG. 5 shows the configuration in which the measured electric resistance value of the skin is converted to a digital value by the analog-digital converter and the voltage is selected, a configuration, in which a voltage is selected by analog circuits, can be used. Such circuits having the above configuration have an advantage in which the configuration of the circuits is simple and low-cost compared with the configuration of the circuits varying the voltage in a continuous manner as described above.

Then, the output unit 104 outputs and apply one or more electroporation voltage pulses having the determined parameters to the skin of the user via the second electrode 112.

FIG. 5 shows an example of voltage pulses output by the measurement unit 102 and the output unit 104 over time. First, the measurement unit 102 outputs one resistance measurement voltage pulse 602 and measures the electric resistance of the skin as described above. Then, the output unit 104 determines, for example, a voltage of the electroporation voltage pulse based on the measured electric resistance value and outputs one electroporation voltage pulse 604 as described above. Then, the measurement unit 102 outputs a next resistance measurement voltage pulse 602' with a predetermined interval after the output of the resistance measurement voltage pulse 602 and measures the electric resistance value of the skin. Then, the output unit 104 determines, for example, the voltage of the electroporation voltage pulse based on the measured electric resistance value and outputs a next electroporation voltage pulse 604' with a predetermined interval after the output of the electroporation voltage pulse 604. Until the output of the pulses is automatically or manually finished, the above cycle is repeated to perform the electroporation method to the skin of the user. Since, in general, an electric resistance value of skin decreases for each application of electroporation voltage pulse as described below, the voltage of the electroporation voltage pulse gradually decreases in order to maintain the current applied to the skin at a predetermined value.

As described above, in the case that the electroporation device is configured to alternatively output the resistance measurement voltage pulse 602 and the electroporation voltage pulse 604 one by one and measure the electric resistance value of the skin for one output of the electroporation voltage pulse, the voltage of the electroporation voltage pulse can be varied to follow the change of the electric resistance of the skin and precisely maintain the current applied to the skin to be a predetermined value. Therefore, discomfort such as a pain sensation to the user can be avoided.

Figure 6:
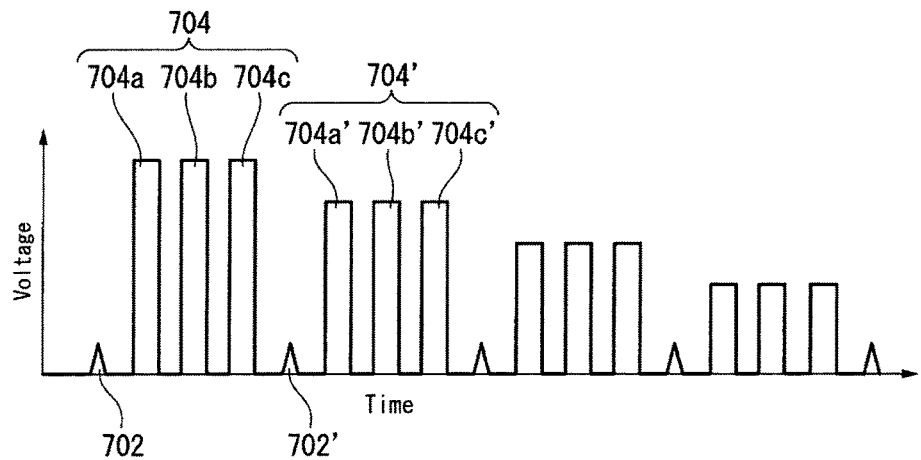
FIG. 6 shows illustrative outputs of resistance measurement voltage pulses and electroporation voltage pulses of the electroporation device according to the embodiment of the present invention.

FIG. 6 shows another example of voltage pulses output by the measurement unit 102 and the output unit 104 over time. First, the measurement unit 102 outputs one resistance measurement voltage pulse 702 and measures the electric resistance value of the skin as described above. Then, the output unit 104 determines, for example, the voltage of the electroporation voltage pulse based on the measured electric resistance value and outputs a bunch of electroporation voltage pulses 704 including a plurality of electroporation voltage pulses 704a, 704b, 704c as described above. Then, the measurement unit 102 outputs a next resistance measurement voltage pulse 702' with a predetermined interval after outputting the resistance measurement voltage pulse 702 and measures the electric resistance value of the skin. Then, the output unit 104 determines, for example, the voltage of the electroporation voltage pulse based on the measured electric resistance value of the skin and outputs a bunch of electroporation voltage pulses 704' including a plurality of electroporation voltage pulses 704a', 704b', 704c' with a predetermined interval after outputting the bunch of electroporation voltage pulses 704. Until the output of the pulses is automatically or manually finished, the above cycle is repeated to perform the electroporation method to the skin of the user. Although FIG. 6 shows the example outputting three electroporation voltage pulses for one resistance measurement voltage pulse, the number of the electroporation voltage pulses in a bunch is not limited to the above example and any numbers of electroporation voltage pulses can be output in a bunch.

As described above, in the case that the electroporation device is configured to output a plurality of electroporation voltage pulses 704 after outputting one resistance measurement voltage pulse 702, the power consumption associated with the output of the resistance measurement voltage pulse, measurement of the electric resistance value, and determination of the voltage of the electroporation voltage pulse can be reduced. Such a configuration is particularly suitable for a case that the change of the electric resistance value of the skin due to output of the electroporation voltage pulses is relatively small.

The output of the resistance measurement voltage pulses and the electroporation voltage pulses is not limited to the above examples but can employ various configurations. For example, the electroporation device can be configured such that output unit 104 outputs one or more electroporation voltage pulses after the measurement unit 102 outputs a plurality of resistance measurement voltage pulses and measures the electric resistance value of the skin. In this case, since the electric resistance value of the skin can be determined by averaging the measurement results obtained by the output of the plurality of resistance measurement voltage pulses, the electric resistance value can be stably determined even if the results of the measurement of the electric resistance value of the skin are unstable.

The output of the resistance measurement of the voltage pulses and the electroporation voltage pulses described above can be controlled by timing instructions output to the measurement unit 102 and the output unit 104 by the microprocessor 106 or the timing unit 108 such as a timer circuit.

The electroporation device and the method for controlling the electroporation device configured as described above can minimize discomfort of the user and facilitate delivering active substances to the skin such as the stratum corneum because the electric resistance value of the skin of the user is measured substantially in real time and the electroporation voltage pulses to be applied are modulated based on the measured electric resistance value.

Figure 7:
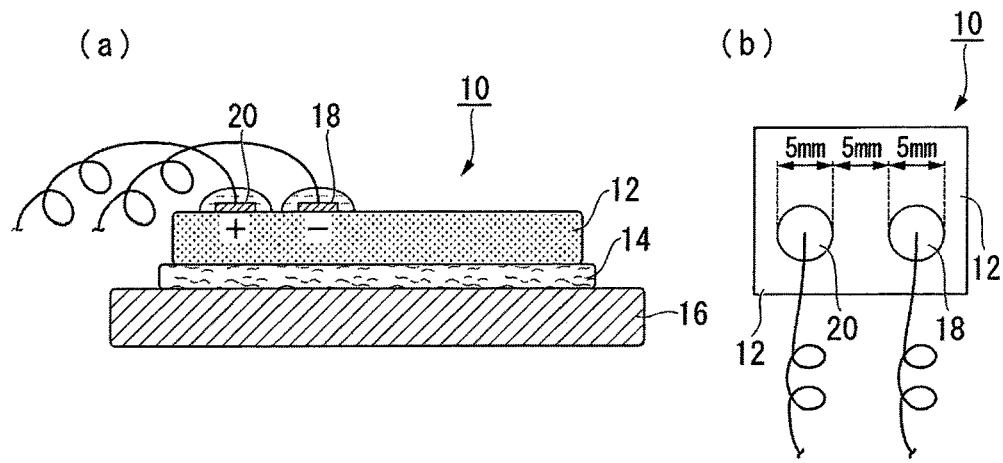
FIG. 7 shows a side view and a plan view of a schematic test system for measuring a variation of an electric resistance value of skin due to applying voltage pulses.

FIG. 7(a) shows a side view of a schematic test system 10 for measuring a variation of an electric resistance value of skin and FIG. 7(b) shows a plan view of the test system 10.

A piece of a porcine ear skin 12, electric characteristics of which are similar to those of a human skin, was disposed on an aluminum heating plate 16 with interposing a sheet of paper 14 including 0.9% NaCl solution. Then, two electrodes 18, 20 were disposed on a surface of the porcine ear skin 12 with a predetermined gap. The electrodes 18, 20 were wetted. Voltage pulses were repeatedly applied between the electrodes 18, 20. Table 1 shows electric resistance values of the porcine ear skin 12 after applying the electric pulses 99 times with a voltage between 5 to 100 V, a duration of 10 milliseconds, an interval of 10 milliseconds, and therefore a pulse duty ratio of 1 as relative values when an electric resistance value before applying the voltage pulses is 100%.

TABLE 1

Variations of the resistance values of the
skin due to applying the voltage pulses
10 milliseconds on/off, 99 times (average of 16 samples)

| | | | | | |
|---|---|---|---|---|---|
| Applied voltage of electroporation voltage pulse (V) | 10 | 20 | 30 | 40 | 50 |
| Variation of electric resistance of skin (%) | 97 | 89 | 74 | 59 | 49 |
| Standard deviation (%) | 2 | 3 | 7 | 4 | 5 |

As shown in Table 1, it was found that the higher the voltage of the applied pulse is, the electric resistance value of the skin decreases.

Table 2 shows electric resistance values of the porcine ear skin 12 after applying the electric pulses 99 times with a voltage of 20 V, a duration between 1 to 10 milliseconds, and a pulse duty ratio of 1, and electric resistance values of the porcine ear skin 12 after application of the voltage pulses with 10 cycles of 99 times as relative values when an electric resistance value before applying the voltage pulses is 100%.

TABLE 2

Variations of the resistance values of the skin
for durations and cycles of the voltage pulses 20 V, 99 times (average of 3 samples)

| | | | |
|---|---|---|---|
| Pulse on/off durations (milliseconds) | 1 | 5 | 10 |
| Variation of electric resistance of skin (%) | 100 | 97 | 89 |
| Standard deviation (%) | 2 | 2 | 3 |

20 V, 10 cycles of 99 times application (average of 3 samples)

| | | | |
|---|---|---|---|
| Pulse on/off durations (milliseconds) | 1 | 2 | 5 |
| Variation of electric resistance of skin (%) | 99 | 89 | 74 |
| Standard deviation (%) | 1 | 3 | 6 |

From the above experimental results, it was found that the electric resistance of the skin gradually decreased in response to the number of the application of the voltage pulses. Therefore, it was found that if voltage pulses based on a predetermined output pattern are applied, an electric resistance of skin of a user gradually decreases. This results in the increase of a current applied to the skin and causes a discomfort even if the user did not feel discomfort when the application of the pulses started. Conventional devices and methods using pulse heights predetermined based on data of preliminarily measured electric resistance of skins to apply voltage pulses to skin of a user based on the pattern data cannot vary parameters of the voltage pulse while applying the voltage pulses, and therefore cannot avoid an increase of discomfort due to an decrease of the electric resistance of the skin. However, since the present invention measures the electric resistance of the skin substantially in real time and varies the parameters of the voltage pluses substantially in real time based on the measurement during applying the electroporation voltage pulses, a current applied to the skin can be maintained at a predetermined value or less and avoid an increase of a discomfort due to a decrease of the electric resistance of the skin.

It should be noted that the foregoing embodiments are merely intended for describing technical solutions of the present invention rather than limiting the present invention. Although the present invention is described in detail with reference to the foregoing embodiments, those skilled in the art should understand that they may still make modifications to the technical solutions recorded in the foregoing embodiments or make equivalent replacements to a part or all of the technical feature thereof.

DESIGNATIONS

10: A test system
12: A porcine ear skin
14: Paper
16: Aluminum heating plate
18, 20: Electrodes
100: An electroporation device
102: A measurement unit
104: An output unit
106: A microprocessor
108: A timing unit
110: A first electrode
112: A second electrode
602, 602': Resistance measurement voltage pulses
604, 604': Electroporation voltage pulses
702, 702': Resistance measurement voltage pulses
704, 704a, 704b, 704c, 704', 704a', 704b', Electroporation voltage pulses

The invention claimed is:

1. An electroporation device comprising:
a measurement unit being configured to provide multiple outputs of one or more resistance measurement voltage pulses for measuring a resistance of skin of a user at a predetermined interval; and
an output unit being configured to provide an output of one or more electroporation voltage pulses to the skin of the user based on the resistance of the skin of the user per each output of the one or more resistance measurement voltage pulses;
wherein the measurement unit is configured to output the resistance measurement voltage pulses having a voltage lower than a voltage of the electroporation voltage pulses.

2. The electroporation device according to claim 1,
wherein the measurement unit is configured to provide multiple outputs of one resistance measurement voltage pulse at a predetermined interval, and
wherein the output unit is configured to provide an output of one electroporation voltage pulse per each output of the one resistance measurement voltage pulse.

3. The electroporation device according to claim 1, wherein the output unit is configured to output the electroporation voltage pulses after varying at least one of a voltage, a pulse duration, an interval between pulses, a number of pulses, and a pulse duty ratio of the electroporation voltage pulse based on the resistance measured by the measurement unit.

4. The electroporation device according to claim 3, wherein the output unit is configured to output the electroporation voltage pulses after varying the voltage of the electroporation voltage pulse based on the resistance measured by the measurement unit.

5. The electroporation device according to claim 4, wherein the output unit is configured to output the electroporation voltage pulses after varying the voltage of the electroporation voltage pulse based on the resistance measured by the measurement unit such that a current applied on the skin of the user by the electroporation voltage pulse is set to be a predetermined value.

6. The electroporation device according to claim 4, wherein the output unit is configured to output the electroporation voltage pulses after varying the voltage of the electroporation voltage pulses in a stepwise manner.

7. The electroporation device according to claim 4, wherein the output unit is configured to output the electroporation voltage pulses after varying the voltage of the electroporation voltage pulses in a continuous manner.

8. The electroporation device according to claim 4, wherein the output unit is configured to output the electroporation voltage pulses after varying the voltage of the electroporation voltage pulses within a range between 5 to 100 V.

9. The electroporation device according to claim 1,
wherein the measurement unit is configured to output the resistance measurement voltage pulses to the skin of the user via a first electrode, and
wherein the output unit is configured to output the electroporation voltage pulses to the skin of the user via a second electrode.

10. The electroporation device according to claim 1, wherein the measurement unit and the output unit are configured to output the resistance measurement voltage pulses and the electroporation voltage pulses to the skin of the user via a common electrode, respectively.

11. The electroporation device according to claim 1, further comprising a timing unit being configured to output timing instructions for outputting the resistance measurement voltage pulses and the electroporation voltage pulses to the measurement unit and the output unit.

12. A method for controlling an electroporation device, comprising:
a step of outputting one or more resistance measurement voltage pulses to skin of a user and measuring a resistance of the skin of the user once for each output of the resistance measurement voltage pulse; and
a step of determining parameters of an electroporation voltage pulse for outputting to the skin of the user once, based on the measured resistance;
wherein the step of outputting the one or more resistance measurement voltage pulses and measuring the resistance of the skin of the user and the step of determining the parameters of the electroporation voltage pulse are repeated; and
wherein a voltage of the resistance measurement voltage pulse is lower than a voltage of the electroporation voltage pulse.

13. The method according to claim 12, wherein the step of outputting the one or more resistance measurement voltage pulses and measuring the resistance of the skin of the user comprises outputting one resistance measurement voltage pulse and one measurement of the resistance of the skin of the user.

14. The method according to claim 12, wherein at least one of a voltage, a pulse duration, an interval between pulses, a number of pulses, and a pulse duty ratio among the parameters of the electroporation voltage pulse is varied based on the measured resistance.

15. The method according to claim 14, wherein the voltage of the electroporation voltage pulse is varied based on the measured resistance.

16. The method according to claim 15, wherein the voltage of the electroporation voltage pulse is varied such that a current applied onto the skin of the user by the electroporation voltage pulse is set to be a predetermined value.

17. The method according to claim 15, wherein the voltage of the electroporation voltage pulse is varied in a stepwise manner.

18. The method according to claim 15, wherein the voltage of the electroporation voltage pulse is varied in a continuous manner.

19. The method according to claim 15, wherein the voltage of the electroporation voltage pulse is varied within a range between 10 and 50 V.

20. The method according to claim 12, wherein the resistance measurement voltage pulses and the electroporation voltage pulses are output in accordance with timing instructions output by a timing unit.

\* \* \* \* \*